United States Patent [19]

Ward et al.

[11] Patent Number: 5,476,928
[45] Date of Patent: * Dec. 19, 1995

[54] MODIFIED NUCLEOTIDES AND POLYNUCLEOTIDES AND COMPLEXES FORM THEREFROM

[75] Inventors: David C. Ward, Guilford, Conn.;
Pennina R. Langer, Monsey, N.Y.;
Alexander A. Waldrop, III,
Charlottesville, Va.

[73] Assignee: Yale University, New Haven, Conn.

[*] Notice: The portion of the term of this patent subsequent to Dec. 8, 2004, has been disclaimed.

[21] Appl. No.: 841,910

[22] Filed: Feb. 26, 1992

Related U.S. Application Data

[60] Continuation of Ser. No. 130,097, Dec. 7, 1987, abandoned, which is a division of Ser. No. 496,915, May 23, 1983, Pat. No. 4,711,955, which is a continuation of Ser. No. 255,223, Apr. 17, 1981, abandoned.

[51] Int. Cl.⁶ .......................... C07H 21/00; C07H 21/02; C07H 19/167; C07H 19/173
[52] U.S. Cl. ............... 536/24; 536/24.31; 536/24.32; 536/26.7; 536/26.8; 536/26.6; 435/6; 436/536
[58] Field of Search ..................... 536/25.30–25.32, 536/26.71, 26.8

[56] References Cited

U.S. PATENT DOCUMENTS

| | | | |
|---|---|---|---|
| 3,328,389 | 6/1967 | Shimizu et al. | 260/211.5 |
| 3,337,530 | 8/1967 | Hanze | 260/211.5 |
| 3,338,882 | 8/1967 | Wechter | 260/211.5 |
| 3,804,826 | 4/1974 | Schelt et al. | 260/211.5 R |
| 3,893,998 | 7/1975 | Secrist, III et al. | 260/211.5 R |
| 3,915,958 | 10/1975 | Shuman et al. | 260/211.5 R |
| 3,917,583 | 11/1975 | Meyer et al. | 260/211.5 R |
| 3,960,840 | 6/1976 | Secrist, III et al. | 260/211.5 R |
| 3,968,101 | 7/1976 | Christensen et al. | 260/211.5 R |
| 4,008,363 | 2/1977 | Re et al. | 536/28 |

(List continued on next page.)

FOREIGN PATENT DOCUMENTS

| | | |
|---|---|---|
| 70687 | 1/1983 | European Pat. Off. |
| 070685 | 1/1983 | European Pat. Off. |
| 2618511 | 11/1976 | Germany |
| 2618419 | 11/1976 | Germany |
| 3045375 | 7/1982 | Germany |
| 4324191 | 10/1943 | Japan ............... 16 E 611.2 |
| 58-62194 | 4/1983 | Japan ............... C07H 19/06 |
| 1548741 | 7/1979 | United Kingdom |
| 1552607 | 9/1979 | United Kingdom |
| 2019408 | 10/1979 | United Kingdom |
| 2026690 | 2/1980 | United Kingdom |
| 1564578 | 4/1980 | United Kingdom |
| 2034323 | 6/1980 | United Kingdom |
| 2041922 | 9/1980 | United Kingdom |
| 2045239 | 10/1980 | United Kingdom |
| 2125964 | 3/1984 | United Kingdom |
| 8302277 | 7/1983 | WIPO ............... C07H 21/00 |
| 8302276 | 7/1983 | WIPO ............... C07H 19/20 |
| 8302286 | 7/1983 | WIPO ............... C12Q 1/68 |

OTHER PUBLICATIONS

Lubert Stryer, Biochemistry, 3rd ed., c. 1975, 1981, 1988 See p. 184, "Formation of an Enzyme–Substrate Complex is the First Step in Enzymatic Catalysis".

(List continued on next page.)

*Primary Examiner*—Douglas W. Robinson
*Assistant Examiner*—Eric Crane
*Attorney, Agent, or Firm*—Ronald C. Fedus; John J. Santalone

[57] ABSTRACT

Compounds having the structure:

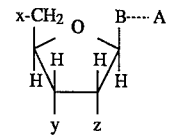

wherein B represents a purine, 7-deazapurine, or pyrimidine moiety covalently bonded to the $C^{1'}$-position of the sugar moiety, provided that when B is purine or 7-deazapurine, it is attached at the $N^9$-position of the purine or 7-deazapurine and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a chemical linkage joining B and A, provided that if B is purine, the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y and z represents

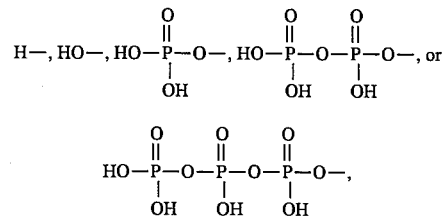

either directly, or when incorporated into oligo- and polynucleotides, provide probes which are widely useful.

Applications include detection and localization of polynucleotide sequences in chromosomes, fixed cells, tissue sections, and cell extracts. Specific applications include chromosomal karyotyping, clinical diagnosis of nucleic acid-containing etiological agents, e.g. bacteria, viruses, or fungi, and diagnosis of genetic disorders.

19 Claims, No Drawings

U.S. PATENT DOCUMENTS

| | | | |
|---|---|---|---|
| 4,038,480 | 7/1977 | Robins et al. | 536/27 |
| 4,048,307 | 9/1977 | Yokota et al. | 424/180 |
| 4,067,774 | 1/1978 | Rubenstein et al. | 195/63 |
| 4,086,417 | 4/1978 | Ishida et al. | 536/29 |
| 4,088,639 | 5/1978 | Zappelli et al. | 260/112.5 R |
| 4,096,324 | 6/1978 | Kelly et al. | 536/23 |
| 4,134,792 | 1/1979 | Boguslaski et al. | 195/99 |
| 4,151,349 | 4/1979 | Traeger et al. | 536/28 |
| 4,171,432 | 10/1979 | Carrico et al. | 536/26 |
| 4,213,893 | 7/1980 | Carrico et al. | 260/112.5 |
| 4,228,237 | 10/1980 | Hevey et al. | 435/7 |
| 4,230,698 | 10/1980 | Bobek et al. | 424/180 |
| 4,230,797 | 10/1980 | Boguslaski et al. | 435/7 |
| 4,247,544 | 1/1981 | Bergstrom et al. | 424/180 |
| 4,261,893 | 4/1981 | Boguslaski et al. | 260/326 N |
| 4,267,171 | 5/1981 | Bergstrom et al. | 424/180 |
| 4,302,204 | 11/1981 | Wahl et al. | 23/230.3 |
| 4,318,980 | 3/1982 | Boguslaski et al. | 435/7 |
| 4,318,981 | 3/1982 | Burd et al. | 435/7 |
| 4,318,982 | 3/1982 | Hornby et al. | 435/7 |
| 4,355,165 | 10/1982 | Boguslaski et al. | 544/237 |
| 4,358,535 | 11/1982 | Falkow et al. | 435/5 |
| 4,363,759 | 12/1982 | Boguslaski et al. | 260/112.7 |
| 4,374,925 | 2/1983 | Litman et al. | 435/7 |
| 4,380,580 | 4/1983 | Boguslaski et al. | 435/7 |
| 4,383,031 | 5/1983 | Boguslaski et al. | 435/7 |
| 4,446,231 | 5/1984 | Self | 435/7 |
| 4,469,863 | 9/1984 | Ts'o et al. | 536/27 |
| 4,581,333 | 4/1986 | Kourilsky et al. | 435/6 |

OTHER PUBLICATIONS

C.-Y. Lee et al. "8–(6-Aminohexyl)–Amino–Adenine Nucleotide Derivatives for Affinity Chromatography," Arch. Biochem. Biophys. 163, pp. 561–569 (1974).

Bergstrom, D. E. and Ruth, J. L., "Synthesis of C–5 Substituted Pyrimidine Nucleosides via Organopalladium Intermediates", JACS 98:6, 1587–1588 (1976).

Bigge, C. F. "Synthesis of 5-Styryl Derivatives of Uracil Nucleosides and Nucleotides", Tetrahedron Letters, 19, 1653–1656 (1979).

Trayer et al., "Preparation of Adenosine Nucleotide Derivatives Suitable for Affinity Chromatography", Biochem. J. (1974) 139:609–623.

U.S. patent application Ser. No. 572,008, Apr. 28, 1975, Boguslaski et al.

E. A. Bayer and M. Wilchek, "The Use of the Avidin–Biotin Complex as a Tool in Molecular Biology," in Methods of Biochemical Analysis, 26, pp. 1–45 (1980).

D. Bergstrom and M. Ogawa, "C–5 Substituted Pyrimidine Nucleosides. 2. Synthesis Via Olefin Coupling To Organopalladium Intermediates Derived From Uridine and 2'–Deoxyuridine", J. Am. Chem. Soc., 100, pp. 8106–8112 (1978).

D. Bergstrom and J. L. Ruth, "Properties of C–5 Mercurated Pyrimidine Nucleosides," J. Carbohydrates, Nucleotides and Nucleosides, 4, pp. 257–289 (1977).

C. F. Bigge et al., "Palladium–Catalyzed Coupling Reactions of Uracil Nucleosides and Nucleotides," J. Am. Chem. Soc., 102, pp. 2033–2038 (1980).

C. Brandon et al., "Structure of a New Pyrimidine from Bacillus subtilis Phage SP-15 Nucleic Acid", Nature New Biology, 239, pp. 70–71 (1972).

T. R. Broker et al., "Electron Microscopic Visualization Of tRNA Genes with Ferritin–Avidin: Biotin Labels," Nucl. Acids Res., 5, pp. 363–383 (1978).

R. M. K. Dale et al., "Direct Covalent Mercuration of Nucleotides and Polynucleotides," Biochemistry, 14, pp. 2447–2457 (1975).

R. M. K. Dale et al., "The Synthesis and Enzymatic Polymerization of Nucleotides Containing Mercury: Potential Tools for Nucleic Acid Sequencing and Structural Analysis", Proc. Natl. Acad. Sci. USA, 70, pp. 2238–2242 (1973).

M. Ya. Feldman, Reactions of Nucleic Acids and Nucleoproteins With Formaldehyde.

J. L. Guesdon et al., "The Use of Avidin–Biotin Interaction In Immunoenzymatic Techniques", J. Histochem. and Cytochem. 27, pp. 1131–1139 (1979).

H. Hayashi and K. Nakanishi, "Synthesis and Absolute Configuration of (+)–5–(4',5'–Dihydroxypentyl)uracil from Bacillus subtilis Phage SP-15 Deoxyribonucleic Acid," J. Am. Chem. Soc., 95, pp. 4081–4083 (1973).

H. Hayashi et al., "Structure and Synthesis of Dihydroxypentyluracil from Bacteriophage SP-15 Deoxyribonucleic Acid," J. Am. Chem. Soc., 95, pp. 8749–8757 (1973).

P. R. Langer et al., "Enzymatic Synthesis of Biotin–Labeled Polynucleotides: Novel Nucleic Acid Affinity Probes", Proc. Natl. Acad. Sci. USA, 78, pp. 6633–6637 (1981).

P. R. Langer and D. C. Ward, "A Rapid and Sensitive Immunological Method For In Situ Gene Mapping," in Developmental Biology Using Purified Genes, ed. D. D. Brown, Academic Press, pp. 647–658 (1981).

P. R. Lange and D. C. Ward, Abstract 1153: "A Rapid and Sensitive Immunological Method For In Situ Gene Mapping," in Journal of Supramolecular Structure and Cellular Biology, ed. Alan R. Liss, Inc. (1981).

Manning et al., "A Method for Gene Enrichment Based on the Avdin–Biotin Interaction. Application to the Drosophila Ribosomal RNA Genes," Biochemistry, 16, pp. 1364–1370 (1977).

M. Pellegrini et al., "Application of the Avidin–Biotin Method of Gene Enrichment to the Isolation of Long Double–Stranded DNA Containing Specific Gene Sequences", Nucl. Acids Res., 4, pp. 2961–2973 (1977).

J. L. Ruth and D. E. Bergstrom, "C–5 Substituted Pyrimidine Nucleosides. 1. Synthesis of C–5 Allyl, Propyl, and Propenyl Uracil and Cytosine Nucleosides via Organopalladium Intermediates," J. Org. Chem., 43, pp. 2870–2876 (1978).

A. Sodja and N. Davidson, "Gene Mapping and Gene Enrichment by the Avidin–Biotin Interaction: Use of Cytochrome–C as a Polyamine Bridge," Nucl. Acids. Res., 5, pp. 383–399 (1978).

M. Swierkowski and D. Shugar, "Poly 5–Ethyluridylic Acid, A Polyuridylic Acid Analogue", J. Mol. Biol., 47, pp. 57–67 (1970).

British Patent Specification No. 1,564,578, Published Apr. 10, 1980 See paragraph spanning pp. 5–6.

The Merck Index, 10 Edition, Merck & Co., Rahway, New Jersey, 1983, see p. 1368, entry 9387.

MODIFIED NUCLEOTIDES AND POLYNUCLEOTIDES AND COMPLEXES FORM THEREFROM

This invention was made with government support under grant numbers P50 GM 20124, T32 GM 07499 and T32 CA 09159 awarded by the National Institutes of Health of the Department of Health and Human Services. The Government has certain rights in the invention. This is continuation of application Ser. No. 07/130,097, filed Dec. 7, 1987, now abandoned, which is in turn a division of application Ser. No. 06/496,915, filed May 23, 1983, issued Dec. 8, 1987 as U.S. Pat. No. 4,711,955, which is in turn a continuation of application Ser. No. 06/255,223, filed Apr. 17, 1981, now abandoned.

BACKGROUND OF THE INVENTION

Many procedures employed in biomedical research and recombinant DNA technology rely heavily on the use of nucleotide of polynucleotide derivatives radioactively labeled with isotopes of hydrogen ($^3$H), phosphorous ($^{32}$p), carbon ($^{14}$C), or iodine ($^{125}$I). Such radioactive compounds provide useful indicator probes that permit the user to detect, monitor, localize, or isolate nucleic acid; and other molecules of scientific or clinical interest, even when present in only extremely small amounts. To date, radioactive materials have provided the most sensitive, and in many cases the only, means to perform many important experimental or analytical tests. There are, however, serious limitations and drawbacks associated with the use of radioactive compounds. First, since personnel who handle radioactive material can be exposed to potentially hazardous levels of radiation, elaborate safety precautions must be maintained during the preparation, utilization, and disposal of the radioisotopes. Secondly, radioactive nucleotides are extremely expensive to purchase and use, in large part due to the cost of equipment and manpower necessary to provide the appropriate safeguards, producer/user health monitoring services, and waste-disposal programs. Thirdly, radioactive materials are often very unstable and have a limited shelf-life, which further increases usage costs. This instability results from radiolytic decomposition, due to the destructive effects associated with the decay of the radioisotope itself, and from the fact that many isotopes e.g. $^{32}$p and $^{125}$I) have half-lives of only a few days.

It is known that haptens can combine with antibodies, but can initiate an immune response only if bound to a carrier. This property can be exploited in detection and identification testing.

It is also known that biotin and iminobiotin strongly interact with avidin, a 68,000 dalton glycoprotein from egg white. This interaction exhibits one of the tightest, non-covalent binding constants ($K_{dis}=10^{-15}$) seen in nature. If avidin is coupled to potentially demonstrable indicator molecules, including fluorescent dyes, e.g. fluorescein or rhodamine; electron-dense reagents, e.g. ferritin, hemocyanin, or colloidal gold; or enzymes capable of depositing insoluble reaction products, e.g. peroxidase or alkaline phosphatase, the presence, location, or quantity of a biotin probe can be established. Although iminobiotin binds avidin less tightly than biotin, similar reactions can be used for its detection. Moreover, the reversibility of the iminobiotin-avidin interaction, by decreasing solution pH, offers significant advantages in certain applications.

The specificity and tenacity of the biotin-avidin complex has been used in recent years to develop methods for visually localizing specific proteins, lipids, or carbohydrates on or within cells (reviewed by E. A. Bayer and M. Wilchek in Methods of Biochemical Analysis, 26, 1, 1980). Chromosomal location of RNA has been determined by electron microscopy using a biotinized protein, cytochrome C, chemically crosslinked to RNA as a hybridization probe. The site of hybridization was visualized through the binding of avidin-ferritin or avidin-methacrylate spheres mediated by the avidin-biotin interaction. (J. E. Manning, N. D. Hershey, T. R. Broker, M. Pellegrini, H. K. Mitchell, and N. Davidson, Chromosoma, 53, 107, 1975; J. E. Manning, M. Pellegrini, and N. Davidson, Biochemistry, 61, 1364, 1977; T. R. Broker, L. M. Angerer, P. H. Yen, N. D. Hersey, and N. Davidson, Nucleic Acid Res., 5, 363, 1978; A Sodja and N. Davidson, Nucleic Acid Res., 5, 383, 1978.) This approach to the detection of polynucleotide sequences, although successful in the specialized cases examined which were highly reitterated sequences, is not of general utility for analysis of polynucleotides present in single or low copy number.

Moreover, methods for attaching chemical moieties to pyrimidine and purine rings are known. Several years ago a simple and rapid acetoxymercuration reaction was developed for introducing covalently bound mercury atoms into the 5-position of the pyrimidine ring, the C-8 position of the purine ring or the C-7 position of a 7-deazapurine ring, both in nucleotides and polynucleotides. (R. M. K. Dale, D. C. Livingston and D. C. Ward, Proc. Natl. Acad. Sci. U.S.A., 70, 2238, 1973; R. M. K. Dale, E. Martin, D. C. Livingston and D. C. Ward, Biochemistry, 14, 2447, 1975.) It was also shown several years ago that organomercurial compounds would react with olefinic compounds in the presence of palladium catalysts to form carbon-carbon bonds (R. F. Heck, J. Am. Chem. Soc., 90, 5518, 1968; R .F. Heck, Ibid., 90, 5526, 1968; R. F. Heck, Ibid., 90, 5531, 1968; R. F. Heck, Ibid., 90, 5535, 1968; and R. F. Heck, J. Am. Chem. Soc. 91, 6707, 1969.) Bergstrom and associates (J. L. Ruth and D. E. Berstrom, J. Org. Chem., 43, 2870, 1978; and D. E. Bergstrom and M. K. Ogawa, J. Am. Chem. Soc., 100, 8106, 1978) and Bigge, et al. (C. F. Bigge, P. Kalaritis, J. R. Deck and M. P. Mertes, J. Am. Chem. Soc., 102, 2033, 1980) have recently applied this reaction scheme in the synthesis of C-5 substituted pyrimidine nucleotide compounds.

Finally, it is known that antibodies specific for modified nucleotides can be prepared and used for isolating and characterizing specific constituents of the modified nucleotides. (T. W. Munns and M. K. Liszewski, Progress in Nucleic Acid Research and Molecular Biology, 24, 109, 1980.) However, none of the antibodies prepared to date against naturally occurring nucleotides have been shown to react with their nucleotide determinant when it exists in a double-stranded RNA or DNA duplex or when in DNA-RNA hybrid molecules.

To circumvent the limitations of radioactively labeled probes or previously utilized chemical and biological probes, a series of novel nucleotide derivatives that contain biotin, iminobiotin, lipoic acid, and other determinants attached covalently to the pyrimidine or purine ring have been synthesized. These nucleotide derivatives, as well as polynucleotides and coenzymes that contain them, will interact specifically and uniquely with proteins such as avidin or antibodies. The interaction between modified nucleotides and specific proteins can be utilized as an alternative to radioisotopes for the detection and localization of nucleic acid components in many of the procedures currently used in biomedical and recombinant-DNA technologies. Methods employing these modified nucleotide-protein interactions have detection capacities equal to or greater than procedures which utilize radioisotopes and they often can be performed more rapidly and with greater resolving power.

These new nucleotide derivatives can be prepared relatively inexpensively by chemical procedures which have been developed and standarized as discussed more fully hereinafter. More significantly, since neither the nucleotide probes of this invention nor the protein reagents employed with them are radioactive, the compounds can be prepared, utilized, and disposed of, without the elaborate safety procedures required for radioisotopic protocols. Moreover, these nucleotide derivatives are chemically stable and can be expected to have functional shelf-lives of several years or more. Finally, these compounds permit the development of safer, more economical, more rapid, and more reproducible research and diagnostic procedures.

SUMMARY OF THE INVENTION

Compounds having the structure:

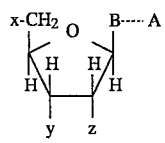

wherein B represents a purine, deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a chemical linkage joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y, and z represents

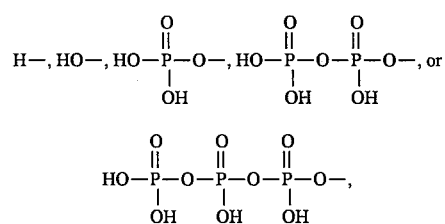

widely useful as probes in biomedical research and recombinant DNA technology.

Particularly useful are compounds encompassed within this structure which additionally have one or more of the following characteristics: A is non-aromatic; A is at least $C_5$; the chemical linkage joining B and A includes an α-olefinic bond; A is biotin or iminobiotin; and B is a pyrimidine or 7-deazapurine.

These compounds may be prepared by a process which involves:

(a) reacting a compound having the structure:

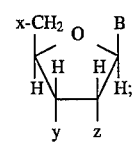

with a mercuric salt in a suitable solvent under suitable conditions so as to form a mercurated compound having the structure:

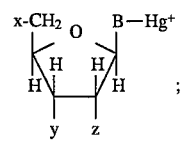

(b) reacting said mercurated compound with a chemical moiety reactive with the $-Hg^+$ portion of said mercurated compound and represented by the formula . . . N, said reaction being carried out in an aqueous solvent and in the presence of $K_2PdCl_4$ under suitable conditions so as to form a compound having the structure:

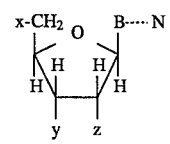

wherein N is a reactive terminal functional group or is A; and (c) recovering said compound as said modified nucleotide when N is A, or when N is a reactive terminal group, reacting said compound with a compound having the structure M-A, wherein M represents a functional group reactive with N in an aqueous solvent under suitable conditions so as to form said modified nucleotide, which is then recovered.

This invention also provides compounds having the structure:

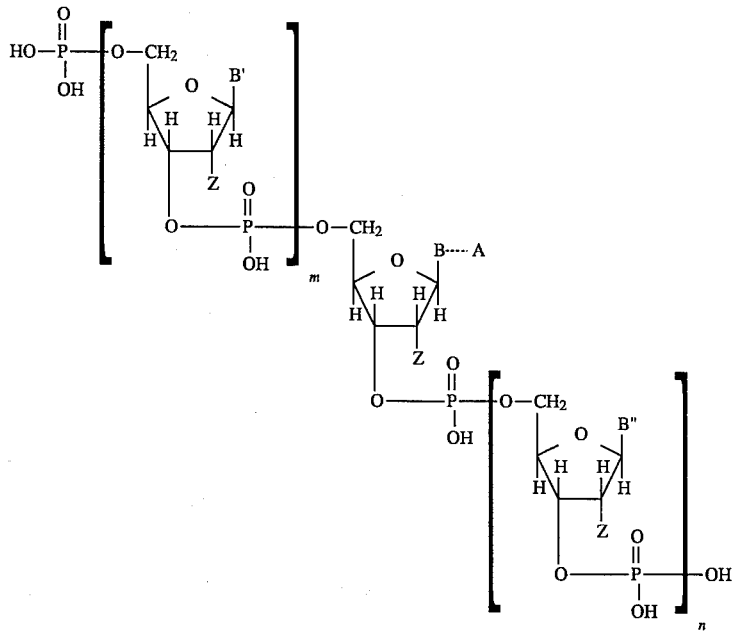

wherein each of B, B', and B" represents a purine, 7-deazapurine, or pyrimidine moiety covalently bonded to the $C^1$-position of the sugar moiety, provided that whenever B, B', or B" is purine or 7-deazapurine, it is attached at the $N^9$-position of the purine or 7-deazapurine, and whenever B, B', or B" is pyrimidine, it is attached at the $N^1$-position;

wherein A represents a moiety consisting of at least three carbon atoms which is capable of forming a detectable complex with a polypeptide when the compound is incorporated into a double-stranded duplex formed with a complementary ribonucleic or deoxyribonucleic acid molecule.

wherein the dotted line represents a chemical linkage joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine;

wherein z represents H— or HO—; and wherein m and n represent integers from 0 up to about 100,000.

These compounds can be prepared by enzymatic polymerization of a mixture of nucleotides which include the modified nucleotides of this invention. Alternatively, nucleotides present in oligo- or polynucleotides may be modified using chemical methods.

Nucleotides modified in accordance with the practices of this invention and oligo- and polynucleotides into which the modified nucleotides have been incorporated may be used as probes in biomedical research, clinical diagnosis, and recombinant DNA technology. These various utilities are based upon the ability of the molecules to form stable complexes with polypeptides which in turn can be detected, either by means of properties inherent in the polypeptide or by means of detectable moieties which are attached to, or which interact with, the polypeptide.

Some uses include detecting and identifying nucleic acid-containing etiological agents, e.g. bacteria and viruses; screening bacteria for antibiotic resistance; diagnosing genetic disorders, e.g. thalassemia and sickle cell anemia; chromosomal karyotyping; and identifying tumor cells.

DETAILED DESCRIPTION OF THE INVENTION

Several essential criteria must be satisfied in order for a modified nucleotide to be generally suitable as a substitute for a radioactively-labeled form of a naturally occurring nucleotide. First, the modified compound must contain a substituent or probe that is unique, i.e., not normally found associated with nucleotides or polynucleotides. Second, the probe must react specifically with chemical or biological reagents to provide a sensitive detection system. Third, the analogs must be relatively efficient substrates for commonly studied nucleic acid enzymes, since numerous practical applications require that the analog be enzymatically metabolized, e.g., the analogs must function as substrates for nucleic acid polymerases. For this purpose, probe moieties should not be placed on ring positions that sterically, or otherwise, interfere with the normal Watson—Crick hydrogen bonding potential of the bases. Otherwise, the substituents will yield compounds that are inactive as polymerase substrates. Substitution at ring positions that alter the normal "anti" nucleoside conformation also must be avoided since such conformational changes usually render nucleotide derivatives unacceptable as polymerase substrates. Normally, such considerations limit substitution positions to the 5-position of a pyrimidine and the 7-position of a purine or a 7-deazapurine.

Fourth, the detection system should be capable of interacting with probe substituents incorporated into both single-stranded and double-stranded polynucleotides in order to be compatible with nucleic acid hybridization methodologies. To satisfy this criterion, it is preferable that the probe moiety be attached to the purine or pyrimidine through a chemical linkage or "linker arm" so that it can readily interact with antibodies, other detector proteins, or chemical reagents.

Fifth, the physical and biochemical properties of polynucleotides containing small numbers of probe substituents should not be significantly altered so that current procedures using radioactive hybridization probes need not be extensively modified. This criterion must be satisfied whether the probe is introduced by enzymatic or direct chemical means.

Finally, the linkage that attaches the probe moiety should withstand all experimental conditions to which normal nucleotides and polynucleotides are routinely subjected, e.g., extended hybridization times at elevated temperatures, phenol and organic solvent extraction, electrophoresis, etc.

All of these criteria are satisfied by the modified nucleotides described herein.

These modified nucleotides have the structure:

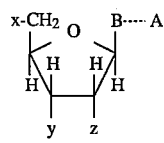

wherein B represents a purine, 7- deazapurine, or pyrimidine moiety covalently bonded to the $C^{1'}$-position of the sugar moiety, provided that when B is purine or 7-deazapurine, it is attached at the $N^9$-position of the purine or 7-deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a linkage group joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y and z represents

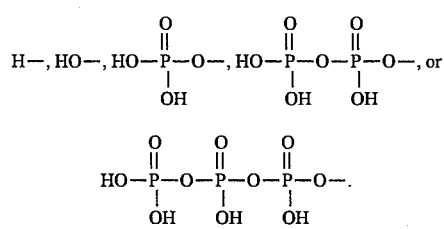

These compounds are widely useful as probes in biomedical research and recombinant DNA technology.

Although in principle all compounds encompassed within this structural formula may be prepared and used in accordance with the practices of this invention, certain of the compounds are more readily prepared or used or both, and therefore are presently preferred.

Thus, although purines, pyrimidines and 7-deazapurines are in principle useful, pyrimidines and 7-deazapurines are preferred since purine substitution at the 8-position tends to render the nucleotides ineffective as polymerase substrates. Thus, although modified purines are useful in certain respects, they are not as generally useful as pyrimidines and 7-deazapurines. Moreover, pyrimidines and 7-deazapurines useful in this invention must not be naturally substituted at the 5- or 7-positions, respectively. As a result, certain bases such as thymine, 5-methylcytosine, and 5-hydroxymethylcytosine are not useful. Presently preferred bases are cytosine, uracil, deazaadenine and deazaguanine.

A may be any moiety which has at least three carbon atoms and is capable of forming a detectable complex with a polypeptide when the modified nucleotide is incorporated into a double-stranded duplex containing either deoxyribonucleic or ribonucleic acid.

A therefore may be any ligand which possesses these properties, including haptens which are only immunogenic when attached to a suitable carrier, but are capable of interracting with appropriate antibodies to produce complexes. Examples of moieties which are useful include:

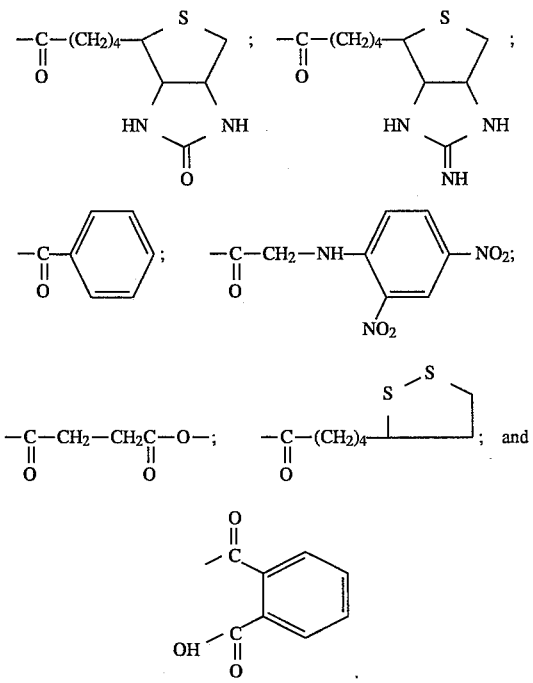

Of these the preferred A moieties are biotin and iminobiotin.

Moreover, since aromatic moieties tend to intercalate into a base-paired helical structure, it is preferred that the moiety A be nonaromatic. Also, since smaller moieties may not permit sufficient molecular interaction with polypeptides, it is preferred that A be at least $C_5$ so that sufficient interaction can occur to permit formation of stable complexes. Biotin and iminobiotin satisfy both of these criteria.

The linkage or group joining moiety A to base B may include any of the well known bonds including carbon-carbon single bonds, carbon-carbon double bonds, carbon-nitrogen single bonds, or carbon-oxygen single bonds. However, it is generally preferred that the chemical linkage include an olefinic bond at the α-position relative to B. The presence of such an α-olefinic bond serves to hold the moiety A away from the base when the base is paired with another in the well known double-helix configuration. This permits interaction with polypeptide to occur more readily, thereby facilitating complex formation. Moreover, single bonds with greater rotational freedom may not always hold the moiety sufficiently apart from the helix to permit recognition by and complex formation with polypeptide.

It is even more preferred that the chemical linkage group be derived from a primary amine, and have the structure —CH$_2$—NH—, since such linkages are easily formed utilizing any of the well known amine modification reactions. Examples of preferred linkages derived from allylamine and allyl-(3-amino-2-hydroxy-1-propyl) ether groups have the formulae

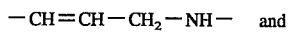

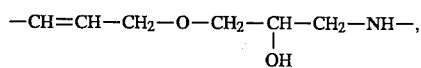

respectively.

Although these linkages are preferred, others can be used, including particularly olefin linkage arms with other modifiable functionalities such as thiol, carboxylic acid, and epoxide functionalities.

The linkage groups are attached at specific positions, namely, the 5-position of a pyrimidine, the 8-position of a purine, or the 7-position of a deazapurine. As indicated previously, substitution at the 8-position of a purine does not produce a modified nucleotide which is useful in all the methods discussed herein. It may be that the 7-position of a purine, which is occupied by a nitrogen atom, could be the point of linkage attachment. However, the chemical substitution methods employed to date and discussed herein are not suitable for this purpose.

The letters x, y, and z represent groups attached to the 5', 3', and 2' positions of the sugar moiety. They may be any of

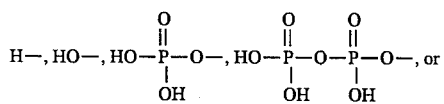

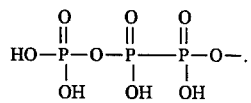

Although conceivable, it is unlikely that all of x, y, and z will simultaneously be the same. More likely at least one of x, y, and z will be a phosphate-containing group, either mono-, di-, or tri-phosphate and at least one will be HO— or H—. As will be readily appreciated, the most likely identity of z will be HO— or H— indicating ribonucleotide or deoxyribonucleotide, respectively. Examples of such nucleotides include 5'-ribonucleoside monophosphates, 5+-ribonucleoside diphosphates, 5'-ribonucleoside triphosphates, 5'-deoxyribonucleoside monophosphates, 5'-deoxyribonucleoside diphosphates, 5'-deoxyribonucleoside triphosphates, 5'p-ribonucleoside-3'p, and 5'p-deoxyribonucleoside-3'p. More specific examples include modified nucleotides of this type in which A is biotin or iminobiotin, the chemical linkage is

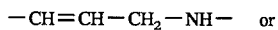

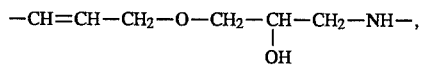

and B is uracil or cytosine.

The general synthetic approach adopted for introducing the linker arm and probe moiety onto the base is discussed hereinabove. (See especially, J. L. Ruth and D. E. Bergstrom, J. Org. Chem., 4.3, 2870, 1978; D. E. Bergstrom and M. K. Ogawa, J. Amer. Chem. Soc. 100, 8106, 1978; and C. F. Bigge, P. Kalaritis, J. R. Deck and M. P. Mertes, J. Amer. Chem. Soc. 102, 2033, 1980.) However, the olefin substituents employed herein have not been used previously. To facilitate attachment of probe moiety A, it has been found particularly desirable to employ olefins with primary amine functional groups, such as allylamine [AA] or allyl-(3-amino-2-hydroxy-1-propyl) ether [NAGE], which permit probe attachment by standard amine modification reactions, such as,

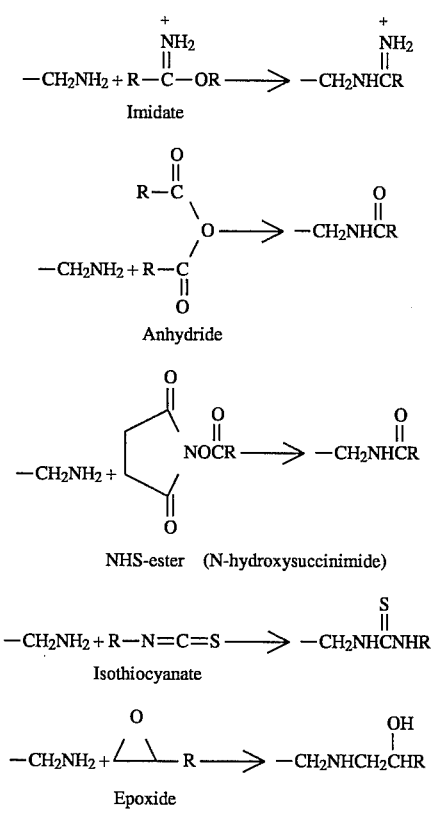

Because of ease of preparation it has been found preferable to use NHS-esters for probe addition. However, olefin linker arms with other modifiable functional groups, such as thiols, carboxylic acids, epoxides, and the like, can also be employed. Furthermore, both linker arm and probe can be added in a single-step if deemed desirable.

Specifically, modified nucleotides having the structure:

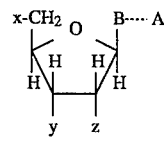

wherein B represents a purine, 7-deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, DNA-RNA hybrid;

wherein the dotted line represents a chemical linkage joining B and A, provided that if B is purine, the linkage is attached to the 8-position of the purine, if 7-deazapurine, the linkage is attached to the 7-position of the deazapurine, and if B is pyrimidine, the linkage is attached to the 5-position of the pyrimidine; and wherein each of x, y, and z represents

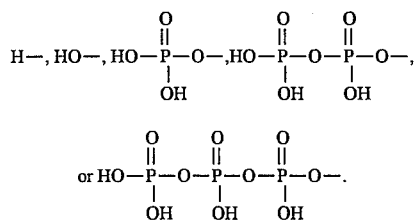

can be prepared by:

(a) reacting a compound having the structure:

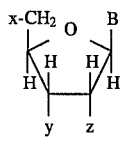

with a mercuric salt in a suitable solvent under suitable conditions so as to form a mercurated compound having the structure:

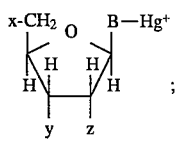

(b) reacting said mercurated compound with a chemical moiety reactive with the —$Hg^+$ portion, of said mercurated compound and represented by the formula ... N, said reaction being carried out in an aqueous solvent and in the presence of $K_2PdCl_4$ under suitable conditions so as to form a compound having the structure:

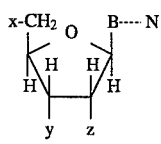

wherein N is a reactive terminal functional group or is A; and (c) recovering said compound as said modified nucleotide when N is A, or when N is a reactive terminal group, reacting said compound with a compound having the structure M-A, wherein M represents a functional group reactive with N in an aqueous solvent under suitable conditions, so as to form said modified nucleotide, which is then recovered.

The following schema is illustrative:

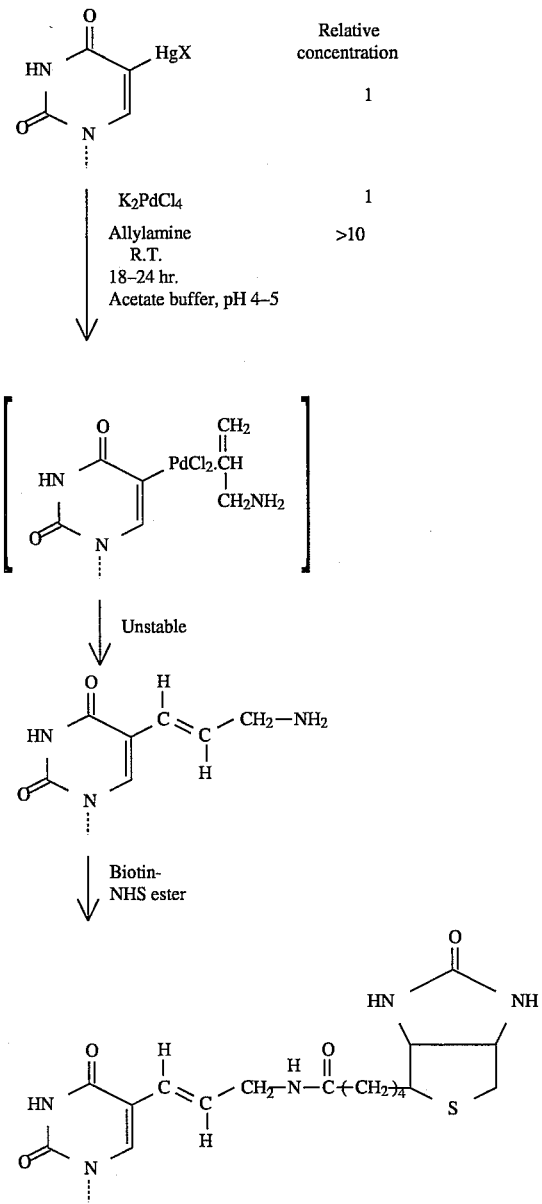

Although the reactions can be carried out at hydrogen ion concentrations as low as pH 1, or as high as pH 14, it is preferred to operate in the range from about 4 to 8. This is especially true when dealing with unstable compounds such as nucleoside polyphosphates, polynucleotides, and nucleotide coenzymes which are hydrolyzed at pH's outside this range. Similarly, it is preferred to operate at a temperature in the range from about 20° C. to 30° C. to avoid possible decomposition of labile organic substrates. However, the reactions can be carried out at temperatures from about 5° C. to 100° C. As is usual with chemical reactions, higher temperatures promote the reaction rate and lower temperatures retard it. Thus, in the temperature range from 5° C. to 100° C., the optimum reaction time may vary from about 10 minutes to 98 hours. In the preferred temperature range, reaction times normally vary from about 3 to 24 hours.

The preferred procedure for maintaining the pH in the desired range is through the use of buffers. A variety of buffers can be employed. These include, for example, sodium or potassium acetate, sodium or potassium citrate, potassium citrate-phosphate, tris-acetate and borate-sodium hydroxide buffers. The concentration of buffer, when employed, can vary over a wide range, up to about 2.0 molar.

While a particular advantage of the mercuration and palladium catalyzed addition reactions is that they can be carried out in water, small amounts of an organic solvent can be usefully included as a solubility aid. The organic solvents usually chosen are those which are miscible with water. These may be selected from ethers, alcohols, esters, ketones, amides, and the like such as methanol, ethanol, propanol, glycerin, dioxane, acetone, pyridine and dimethylformamide. However, since it has been observed that the presence of alcohols, such as methanol, often results in alkoxy-addition across the olefin double bond, any organic solvent used as a solubility aid should be chosen carefully. Introduction of alkoxy substituents to the $\alpha$- or $\beta$-exocyclic carbon atoms often results in the production of compounds which are utilized much less efficiently as enzyme substrates.

Although various mercuric salts may be utilized, the presently preferred salt is mercuric acetate. Also, as indicated previously, the compounds may be prepared by first adding a linker arm and then the moiety A, or by adding a linker arm to which A is already attached. Thus, the chemical moiety represented by the formula . . . N may be any one of the numerous entities which ultimately result in production of the desired compounds.

Examples include

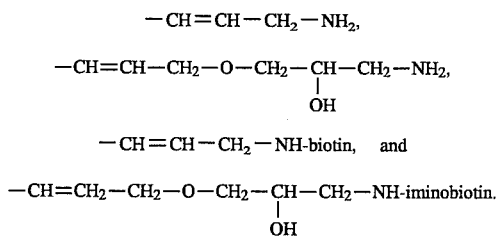

The amounts of the reactants employed in these reactions may vary widely. However, in general the amounts of unmercurated compound, mercurated compound, and palladium-containing compound will be substantially stoichiometric whereas the mercuric salt and compound . . . N will be present in molar excess, e.g. 5–20 moles of . . . N or of mercuric salt per mole of mercurated compound or unmercurated compound, respectively. In practice, amounts will vary depending upon variations in reaction conditions and the precise identity of the reactants.

Having the biotin probe directly attached to nucleotide derivatives that are capable of functioning as enzyme substrates offers considerable versatility, both in the experimental protocols that can be performed and in the detection methods (microscopic and non-microscopic) that can be utilized for analysis. For example, biotin nucleotides can be introduced into polynucleotides which are in the process of being synthesized by cells or crude cell extracts, thus making it possible to detect and/or isolate nascent (growing) polynucleotide chains. Such a procedure is impossible to do by any direct chemical modification method. Furthermore, enzymes can be used as reagents for introducing probes such as biotin into highly selective or site-specific locations in polynucleotides; the chemical synthesis of similar probe-modified products would be extremely difficult to achieve at best.

The synthesis of nucleotides containing biotin or iminobiotin was achieved as detailed in the examples set forth hereinafter. Pyrimidine nucleoside triphosphates containing either of these probes attached to the C-5 carbon atom were good to excellent substrates for a wide variety of purified nucleic acid polymerases of both prokaryotic and eukaryotic origin. These include DNA polymerase I of *E. coli*, bacteriophage T4 DNA polymerase, DNA polymerases $\alpha$ and $\beta$ from murine (A-9) and human (HeLa) cells, and the DNA polymerase of Herpes simplex virus. Confirming data were obtained with *E. coli* DNA polymerase I using either the nick-translation condition of Rigby, et al. (P. W. J. Rigby, M. Dieckmann, C. Rhodes and P. Berg, J. Mol. Biol. 113, 237, 1977) or the gap-filling reaction described by Bourguignon et al. (G. J. Bourguignon, P. J. Tattersall and D. C. Ward, J. Virol. 20, 290, 1976). Bio-dUTP has also been found to function as a polymerase substrate both in CHO cells, permeabilized by treatment with lysolecithin according to the method of Miller, et al. (M. R. Miller, J. C. Casteliot, Jr. and A. B. Pardee, Exp. Cell Res. 120,421, 1979) and in a nuclear replication system prepared from Herpes simplex infected BHK cells. Although biotinyl ribonucleoside triphosphates were found to function as substrates for the RNA polymerases of *E. coli* and bacteriophage T7, they are not utilized as efficiently as their deoxyribonucleotide triphosphate counterparts. Indeed, they are incorporated poorly, if at all, by the eukaryotic RNA polymerases examined (HeLa cell RNA polymerase III, calf thymus RNA polymerase II and mouse cell RNA polymerase II). While this limited range of substrate function does restrict the utility in some in vivo or in vitro transcription studies, biotinlabeled RNA probes can be prepared enzymatically from DNA templates using *E. coli* or T7 RNA polymerases or by 3' end-labeling methods using RNA ligase with compounds such as biotinyl-pCp. The AA- and NAGE-derivatives of UTP are, however, substrates for the eukaryotic RNA polymerases mentioned above. With the availability of antibodies to these analogs, the isolation of nascent transcripts by immunological or affinity procedures should be feasible.

The enzymatic polymerization of nucleotides containing biotin or iminobiotin substituents was not monitored directly, since neither of these probes were radiolabeled. However, two lines of experimental evidence clearly show that the biotinyl-nucleotides were incorporated. The first is that polynucleotides synthesized in the presence of biotin-nucleotides are selectively retained when chromatographed over avidin or streptavidin affinity columns. (Tables I and II) For example, whereas normal DNA, nick translated with $^{32}$P-dAMP, is quantitatively eluted upon the addition of 0.5M NaCl, the vast majority of biotinyl-DNA or iminobiotinyl-DNA remains bound to the resin even after extensive washing with high salt, urea, quanidine-HCl, formamide or 50 mM NaOH. The small fraction of the radiolabel eluted by these washing conditions is not retained when applied to the resin a second time, suggesting that radioactivity is associated with DNA fragments which are free of biotin substitution. The second line of evidence is that only biotin-labeled polynucleotides are immunoprecipitated when treated with purified anti-biotin IgG followed by formalin-fixed *Staphylococcus aureus*. (Table III) It is clear from the data in these tables that extremely small amounts of biotin can be detected by this method. These results also show that the biotin molecule can be recognized by avidin, streptavidin or specific antibodies while the DNA is still in its native, double-stranded form, a condition that is absolutely essential if the antibody-binding or avidin-affinity approaches are to be useful in probe detection employing hybridization techniques.

TABLE I

SELECTIVE RETENTION OF BIOTINIZED DNA ON AVIDIN-SEPHAROSE

| | | % DNA Retained on Resin | |
|---|---|---|---|
| Eluent | | Bio-DNA (1%) | T-DNA |
| Load - | $3 \times 10^5$ cpm 10 mM Tris 7.5 + 0.2 M NaCl | 100 | 100% |
| (1) | 0.5 M NaCl | 100 | 0.1 |
| (2) | 1.0 M NaCl | 99.7 | <0.01 |
| (3) | 8 M Urea | 100 | <0.01 |
| (4) | 6 M guanidine-HCl | 95.2 | <0.01 |
| (5) | 99% formamide | 94.7 | <0.01 |
| (6) | 2 mM Biotin | 97.6 | <0.01 |
| (7) | 50 mM NaOH | 89.5 | <0.01 |

TABLE II

Affinity Chromatography of Iminobiotin-dUTP and Iminobiotinized - DNA on Streptavidin-Sepharose

| | | % Retained on SA-Sepharose | | |
|---|---|---|---|---|
| Eluent | | T-DNA | $^3$H-IB-dUTP | IB-DNA |
| Load - | 10 mM Tris-HCl, 8.3 50 mM NaCl | 8.7 | 100 | 99.7 |
| (1) | 0.1 M NaCl | <0.1 | 100 | 99.7 |
| (2) | 1.0 M NaCl | <0.01 | 100 | 99.4 |
| (3) | 8 M Urea | <0.01 | 97.5 | 98.5 |
| (4) | 6 M guanidine-HCl | <0.01 | 97.0 | 97.0 |
| (5) | 50 mM NH$_4$-acetate, pH 4.0 | <0.01 | <0.01 | 96.5 |
| (6) | 50 mM NH$_4$-acetate, pH 4.0 2 mM biotin | <0.01 | <0.01 | <0.01 |

TABLE III

**SELECTIVE IMMUNOPRECIPITATION OF BIO-DNA WITH ANTI-BIOTIN IgG and *STAPH AUREUS***

| DNA* | Antibody | CPM in Immuno ppt. | CPM in Supernatant |
|---|---|---|---|
| T-DNA | — | 70 | 4867 |
| T-DNA | Anti-Bio IgG | 87 | 5197 |
| T-DNA | Non-immune IgG | 55 | 5107 |
| Bio-DNA | — | 53 | 3886 |
| Bio-DNA | Anti-Bio IgG | 3347 | 736 |
| Bio-DNA | Non-immune IgG | 60 | 3900 |

*N.T. pBR-322 DNA, $^{32}$p-labeled; 1% Biotin substitution. Specific activity, $2 \times 10^7$ cpm/µg Biotin detection 0.001–0.01 pmoles.

Thus, it is possible to prepare novel compounds having the structure:

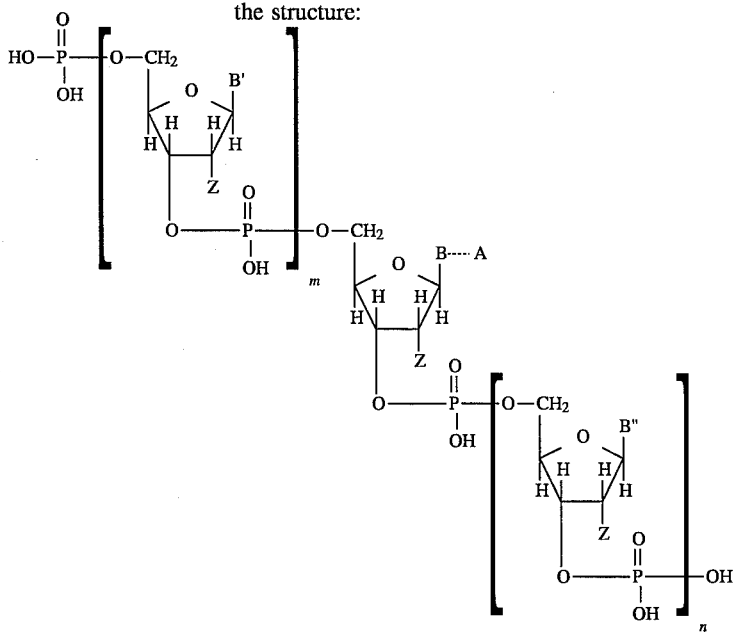

wherein each of B, B' and B", represents a purine, deazapurine, or pyrimidine moiety covalently bonded to the $C^{1'}$-position of the sugar moiety, provided that whenever B, B', or B" is purine or 7-deazapurine, it is attached at the $N^9$-position of the purine or deazapurine, and whenever B, B', or B" is pyrimidine, it is attached at the $N^1$-position;

wherein A represents a moiety consisting of at least three carbon atoms which is capable of forming a detectable complex with a polypeptide when the compound is incorporated into a double-stranded duplex formed with a complementary ribonucleic or deoxyribonucleic acid molecule.

wherein the dotted line represents a linkage group joining B and A, provided that if B is purine, the linkage is attached to the 8-position of the purine, if B is 7-deazapurine, the linkage is attached to the 7-position of the deazapurine, and if B is pyrimidine, the linkage is attached to the 5-position of the pyrimidine;

wherein z represents H— or HO—; and wherein m and n represent integers from 0 up to about 100,000.

Of course, it should be readily understood that in general m and n will not simultaneously be 0 since, in that event, the compound becomes merely a modified nucleotide as described previously. In general B' and B" will vary within the same oligo- or polynucleotide, being alternatively uracil, cytosine, thymine, guanine, adenine, or the like. Also, in general, the variation will correspond to the ordered sequence of nucleotides which codes for the synthesis of peptides according to the well known Genetic Code. However, it is intended that the structure shown also embrace polynucleotides such as poly C, poly U, poly r(A-U), and poly d(A-U) as well as calf thymus DNA, ribosomal RNA of $E.\ coli$ or yeast, bacteriophage RNA and DNA (R17, fd), animal viruses (SV40 DNA), chromosomal DNA, and the like, provided only that the polynucleotides be modified in accordance with this invention.

It is also to be understood that the structure embraces more than one modified nucleotide present in the oligomer or polymer, for example, from two to thirty modified nucleotides. The critical factor in this regard is that the number of modifications not be so great that the polynucleotide is rendered ineffective for the intended use.

Finally, it should be understood that modified oligo- and polynucleotides can be joined to form larger entities having the same structure so long as terminal groups are rendered compatible or reactive.

These compounds can be made by enzymatic polymerization of appropriate nucleotides, especially nucleotide triphosphates in the presence of a nucleic acid template which directs synthesis under suitable conditions. Such conditions can vary widely depending upon the enzyme employed, amounts of nucleotides present, and other variables. Illustrative enzymes include DNA polymerase I of $E.\ coli$, bacteriophage T4 DNA polymerase, DNA polymerases α and β from murine and human (HeLa) cells, DNA polymerase from Herpes simplex virus, RNA polymerase of $E.\ coli$, RNA polymerase of bacteriophage T7, eukaryotic RNA polymerase including HeLa cell RNA polymerase III, calf thymus RNA polymerase II, and mouse cell RNA polymerase II.

Also, the compounds can be prepared by terminal addition to oligo- or polynucleotides to produce compounds in which m or n is 0 depending upon whether the addition is at the 5' or 3' position. Moreover, the compounds such as pCp or pUp in which the base is biotinized can be added to existing molecules employing the enzyme RNA ligase.

Modified oligo- and polynucleotides can also be prepared by chemical modification of existing oligo- or polynucleotides using the approach described previously for modification of individual nucleotides.

The various modified nucleotides, oligonucleotides, and polynucleotides of this invention may be detected by contacting the compounds with polypeptides which are capable of forming complexes therewith under suitable conditions so as to form the complexes, provided that the polypeptides include one or more moieties which can be detected when the complex or complexes is or are formed, generally by means of conventional detection techniques.

One polypeptide detector for the biotinyl-type probe is avidin. The avidin-biotin interaction exhibits one of the tightest non-covalent binding constants ($K_{dis}=10^{-15}$) seen in nature. If avidin is coupled to potentially demonstrable indicator molecules, e.g., fluorescent dyes (fluoroscein, rhodamine), electron-dense reagents (ferritin, hemocyanin, colloidal gold), or enzymes capable of depositing insoluble reaction products (peroxidase, alkaline phosphatase) the presence, location and/or quantity of the biotin probe can be established.

Avidin has, unfortunately, one property that makes it less desirable as a biotin-indicator protein when used in conjunction with nucleic acids or chromatin material. It has been reported (M. H. Heggeness, Stain Technol., 52, 165, 1977; M. H. Heggeness and J. F. Ash, J. Cell. Biol., 73, 783, 1977; E. A. Bayer and M. Wilchek, Methods of Biochemical Analysis 26, 1, 1980) that avidin binds tightly to condensed chromatin or to subcellular fractions that contain large amounts of nucleic acid in a manner which is independent of its biotin-binding property. Since avidin is a basic glycoprotein with a pI of 10.5, its histone-like character or its carbohydrate moieties are most likely responsible for these observed non-specific interactions.

A preferred probe for biotin-containing nucleotides and derivatives is streptavidin, an avidin-like protein synthesized by the soil organism $Streptomyces\ avidinii$. Its preparation and purification is described in Hoffman, et al., Proc. Natl. Acad. Sci., 77, 4666 (1980). Streptavidin has a much lower pI (5.0), is non-glycosylated, and shows much lower non-specific binding to DNA than avidin, and therefore offers potential advantages in applications involving nucleic acid detection methodology.

A most preferred protein for biotin-like probe detection is monospecific rabbit IgG, antibiotin immunoglobulin. This compound was prepared by immunizing rabbits with bovine serum albumin conjugated biotin as described previously (M. Berger, Methods in Enzymology, 62, 319[1979]) and purified by affinity chromatography. Although the association constant of immunoglobulin-haptens have values of $K_{assn}$ ($10^6$ to $10^{10}$) which are considerably lower than for avidin-biotin complexes, they are substantially equivalent to those observed with the avidin-iminobiotin complex. Furthermore, the anti-biotin antibodies have proven extremely useful in detecting specific polynucleotide sequences on chromosomes by in situ hybridization since little, if any, non-specific binding of the antibody to chromatin material occurs.

The modified polynucleotides of this invention are capable of denaturation and renaturation under conditions compatible with their use as hybridization probes. An analysis of the thermal denaturation profiles and hybridization properties of several biotin-substituted DNA and RNA polymers clearly indicates this. For example, pBR 322 DNA or λ DNA, nick translated to introduce approximately 10–100 biotin residues per kilobase, have Tm values essentially identical to that of the control, biotin-free DNAs. Furthermore, $^{32}$P-labeled, biotin-substituted, pBR 322 DNA, exhibited the same degree of specificity and autoradiographic signal intensity as control, thymidine-containing DNA, when used as a hybridization probe for detecting bacterial colonies containing the plasmid.

In DNA duplexes, such as MVM RF DNA, in which every thymidine residue in one strand (1250 in toto per 5 Kb) is replaced by a biotinyl-nucleotide, the Tm is only 5° C. less than that of the unsubstituted control. Although the Tm of poly d(A-bioU) in which each base pair contains a bio-dUMP residue is 15° C. lower than the poly d(A-T) control, the degree of cooperativity and the extent of hyperchromicity observed both during denaturation and renaturation were the same for the two polymers. A parallel analysis of RNA duplexes and DNA/RNA hybrids indicates that their Tm's also decrease as the biotin-content of the polymer increases. However, it is clear that a substantial number of biotinmolecules can be introduced without significantly altering the hybridization characteristics of the polymers.

These results strongly suggested that biotin-substituted polynucleotides could be used as probes for detecting and/or localizing specific polynucleotide sequences in chromosomes, fixed cells, or tissue sections. The general protocol for detecting the biotin-substituted probe is schematically illustrated as follows:

GENERAL PROTOCOL FOR PROBE DETECTION
VIA IN SITU, COLONY, OR NORTHERN/SOUTHERN
HYBRIDIZATION METHODS

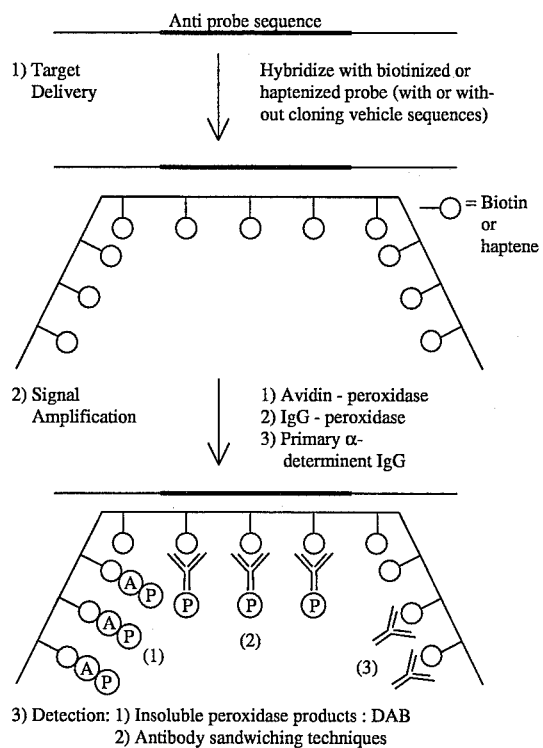

3) Detection: 1) Insoluble peroxidase products : DAB
2) Antibody sandwiching techniques This general scheme illustrates only procedures used for gene mapping (cytogenetics), and recombinant DNA-technologies. However, it can be equally well applied to the detection of nucleic acid sequences of bacterial, viral, fungal or parasite origin in clinical samples and this forms the basis of a powerful new approach to clinical diagnostics which does not rely on the use of radioisotopes.

Immunological and histochemical methods for the detection of biotin have shown that the basic approach is useable for a rapid method of gene mapping in situ hybridization and non-radioactive procedures for detecting specific nucleic acid sequences by blotting hybridization methods. Use may be made of this technology in development of new clinical diagnostic procedures.

Using this approach, it is possible to determine the presence of a specific deoxyribonucleic or ribonucleic acid molecule, particularly such a molecule derived from a living organism, e.g. bacteria, fungus, virus, yeast, or mammal. This in turn permits diagnosis of nucleic acid-containing etiological agents in a patient or other subject.

Moreover, it provides a method for screening bacteria to determine antibiotic resistance. Thus, for example, penicillin resistance in *Streptococcus pyogenes* or *Neisseris meningitidis*; tetracycline resistance in *Staphylococcus aureus, Candida albicans, Pseudomonas aeruqinosa, Streptococcus pyogenes,* or *Neisseria gonorrhoeae*; and aminoglycoside resistance in *Mycobacterium tuberculosis* can be determined.

In these methods a polynucleotide is prepared which is complementary to the nucleic acid sequence which characterizes the organism or its antibiotic resistance and which additionally includes one or more modified nucleotides according to this invention. This polynucleotide is hybridized with nucleic acid obtained from the organism under scrutiny. Failure to hybridize indicates absence of the organism or of the resistance characteristic. Hybridized nucleic acid duplexes are then identified by forming a complex between the duplex and a suitable polypeptide which carries a detectable moiety, and detecting the presence of the complex using an appropriate detection technique. Positive detection indicates that the complex, the duplex and therefore the nucleic acid sequence of interest are present.

This approach can be extended to the diagnosis of genetic disorders, such as thalassemia and sickle cell anemia. The deoxyribonucleotide acid gene sequence whose presence or absence (in the case of thalassemia) is associated with the disorder can be detected following hybridization with a polynucleotide probe according to this invention based upon complex formation with a suitable detectable polypeptide.

The mapping of genes or their transcripts to specific loci on chromosomes has been a tedious and time-consuming occupation, involving mainly techniques of cell-fusion and somatic cell genetics. Although in situ hybridization has been employed successfully for mapping single-copy gene sequences in species that undergo chromosomes polytenization, such as Drosophila, detection of unique sequence genes in most higher eukaryotic chromosomes has been extremely difficult, if not impossible, using standard hybrization methods. The necessity for polynucleotide probes of very high specific radioactivity to facilitate autoradiographic localization of the hybridization site also results in rapid radiodecomposition of the probe and a concomitant increase in the background noise of silver grain deposition. The use of hybridization probes with low to moderate specific radioactivities requires exposure times of many days or weeks, even to detect multi-copy sequences, such as ribosomal RNA genes or satellite DNA. Since recombinant DNA technology has made feasible the molecular cloning of virtually every single-copy sequence found in eukaryotic cells, it would be extremely beneficial to have a rapid and sensitive method for mapping the chromosmal origin of such cloned genomic fragments.

Modified nucleotides may be used in a method of gene mapping by in situ hybridization which circumvents the use of radioisotopes. This procedure takes advantage of a thymidine analogue containing biotin that can be incorporated enzymatically into DNA probes by nick translation. After hybridization in situ the biotin molecules serve as antigens for affinity purified rabbit anti-biotin antibodies. Immunofluorescent antibody sandwiches made with fluorescein-labeled goat anti-rabbit IgG allow for rapid and specific cytogenetic localization of cloned gene sequences as green-yellow bands. This method offers four major advantages over conventional autoradiographic methods of in situ gene localization; less background noise, an increase in resolving power between bands; a decrease in the time required to determine the site of probe hybridization; and chemically stable hybridization probes. This method has been applied successfully to the localization of reiterated and unique DNA sequences in the polytene chromosome of *Drosophila milanogaster* and satellite DNA on mouse metaphase chromosomes.

Thus it has been found that polytene chromosomes could be used as a test system for establishing the efficacy of probes using the modified nucleotides according to the instant invention as detected by indirect immunofluorescence for in situ gene mapping. The probes included a variety of cloned Drosophila sequences obtained from Otto Schmidt and Dieter Söll, such as tRNA genes cloned in plasmid vectors with inserts of sizes ranging from about 5 to about 22 kilobases. Many of these clones have already been assigned to specific bands on the Drosophila chromosome map by conventional in situ hybridization methods employing radioisotopes.

DNA probes were nick translated in the presence of Bio-dUTP. Occasionally $^3$H dATP and/or $^3$H dCTP was included in the nick translation reaction mixture. This allowed both autoradiographic and immunofluorescent localization of a sequence on a single chromosome spread. In situ hybridization was performed as described in M. L. Pardue, and J. G. Gall, Methods in Cell Biol., 10, 1 (1975). After the final 2×SSC wash to remove unhybridized probe, the slides were rinsed with PBS (phosphate buffered saline) and incubated at 37° C. with 2.5 µg/ml Rabbit anti-biotin in PBS and 10 mg/ml BSA for 2–16 hours. This was followed by incubation of the slides with FITC labeled Goat anti-Rabbit IgG (Miles Laboratories, diluted 1:100 in PBS and 10 mg/ml BSA) for one-four hours. Evans Blue was often required as a red counterstain to see the chromosomes with fluorescent illumination.

When plasmids pBR 17D and pPW 539 containing 5 Kb and 22 Kb inserts, respectively, were hybridized by this method, it was found that the pattern of hybridization is reproducible from spread to spread and is observed unambiguously on greater than 90% of the chromosome spreads on a given slide.

The cloned transposable element pAC 104 is known to map at many sites along the Drosophila genome. Comparison of the autoradiograph and the fluorescent picture obtained by in situ hybridization of this probe illustrates a major advantage of this method, i.e., that where diffuse regions of silver grains appear on an autoradiograph, doublets or a series of bands are discernible by immunofluorescent labeling.

The other immediately obvious advantage of this method is the tremendous decrease in time required for gene assignments to be made by indirect immunofluorescence. An assignment of a DNA fragment to a specific band can be made within six hours of hybridization. This is in comparison to days or weeks required for autoradiographic exposure methods. This factor, in combination with increased resolution, makes the use of modified nucleotides detected by indirect immunofluorescence immediately preferable to more classical methods.

It has been shown that this immunological method also works with mammalian chromosomes wherein satellite DNA has been mapped to the centromeric regions of mouse metaphase chromosomes. The result provides a basic foundation for the development of a simple gene mapping procedure for single copy (unique) sequences in chromosomes from human and other mammals. Such a procedure should greatly facilitate our understanding of the genetic organization of the chromosome and make clinical cytogenetic diagnosis much more rapid and practical.

While a single-step "antibody sandwich" method in which the chromosome spread is challenged, post-hybridization, with rabbit anti-biotin IgG may succeed, this protocol may not generate sufficient fluorescence for unambiguous gene assignments. However, a much stronger fluorometric signal can be achieved by using the "haptene-antibody sandwich technique" described by Lamm, et al., (1972); Wofsy, et al., (1974). In this procedure the primary antibody, in our case monospecific, rabbit anti-biotin IgG, is chemically modified with a haptenization reagent, such as 2,4-dinitrofluorobenzene, preferably while the immunoglobulin is bound to an antigen affinity column (biotin-Sepharose TM). As many as 15–20 haptene (DNP) groups can be coupled to the primary antibody without decreasing its antigen binding affinity or specificity (Wallace and Wofsy, 1979). If the primary antibody treatment of the test sample is followed by an incubation with a fluorescently labeled anti-hapten IgG antibody, rather than a fluorescently labeled anti-IgG, a 5–7 fold increase in fluorescence signal can be achieved. Since one also has available monospecific guinea pig anti-DNP IgG, we can haptenize this secondary antibody with biotin and thus generate two anti-hapten IgG populations, DNP-labeled anti-biotin IgG and biotin-labeled anti-DNP IgG. If these can be used alternately to achieve several rounds of hapten-antibody sandwiching and then followed with fluorescently labeled protein A from *Staphylococcus aureus*, which binds specifically to IgG molecules from many mammalian species, it could result in an enormous amplification of the primary antibody signal with its concomitant utility.

The protein streptavidin from *Streptomyces avidini* is a potential alternative to anti-biotin IgG as a vehicle to specifically direct a coupled visualization system [e.g., fluorescent probes (above) or histochemical reagents (below)] to the site of the hybridized biotin-containing polynucleotide. One of streptavidin's advantages over anti-biotin IgG is that its affinity for biotin is $K_{assn}=10^{15}$ whereas association constants for haptene-IgG interactions are $10^7$ to $10^{10}$. The fast reaction rate and extreme affinity mean that the time required to localize the biotinized probe will be minutes with streptavidin versus hours with immunologic reagents.

Initial evaluations of a streptavidin detection system are currently in progress. Polytene chromosomes hybridized with biotinized DNA probes will be incubated with streptavidin followed by a subsequent incubation with bovine serum albumin which has been doubly labeled with biotin and FITC (FITC, biotinyl-BSA). Since only one of the four streptavidin subunits is likely to be involved in binding at each biotinized DNA site, potentially one labeled BSA molecule can bind to each of the remaining three nonconjugated subunits of the streptavidin-biotinyl nucleotide complex. The fluorescence signal from this single streptavidin+FITC, biotinyl-BSA layer will be compared with a control using the basic "antibody sandwich method" described earlier.

If the "antibody sandwich" and streptavidin+FITC, biotinyl-BSA detection intensities are comparable, one can attempt to enhance the streptavidin+FITC, biotinyl-BSA system to single-copy copy sensitivity in a manner that parallels the multiple "haptene-antibody sandwich" approach. Since some of biotin groups on BSA will not be bound to the first layer of streptavidin, a second layer of streptavidin can be added until sufficient signal is obtained. For example, if in the second layer, only two streptavidin protomers bind to each first-layer BSA and each of these streptavidin protomers binds three FITC-biotinyl BSA molecules, then the second layer intensity will be twice as great as that from the first layer; for the third layer, with analogous binding stoichiometries, the fluorescent intensity will be 12-fold that of the first layer, so the total intensity will rapidly increase With successively added layers. There are plans to use a larger carrier protein such as thyroglobulin rather than BSA in order to maximize amounts of attached fluorescent and biotin probes. It may also be necessary to use a longer linker arm between the biotin probe and the carrier protein. A longer linker arm should sterically optimize the theoretical delivery of a biotinized fluorescent carrier molecule to each nonconjugated streptavidin subunit and maximize the number of streptavidin protomers in the subsequent layer which will bind to the biotinized fluorescent carrier. As before, appropriate controls will be done to insure that substitution of the carrier protein with fluorescent probes and biotin does not cause solubility and/or nonspecific binding problems.

The streptavidin-carrier protein delivery system has two significant advantages over the immunfluorescent approach in addition to its speed of delivery. First, only two protein components are needed to form the layers. Second, only the carrier protein needs to be modified and it is not necessary to maintain functional or even total structural integrity as long as the biotin groups are accessible to streptavidin.

An alternative to the fluorescence method for visualizing hybridized probes is to direct enzymes such as peroxidase, alkaline phosphatase of β-galactosidase to the hybridization site where enzymatic conversion of soluble substrates to insoluble colored precipitates permits light microscope visualization. The important advantage of this technique is that the histochemical methods are 10 to 100-fold more sensitive than fluorescence-detection. In addition, the colored precipitates do not bleach with extensive light exposure thus avoiding one of the general disadvantages of fluorescent light microscopy. These enzymes can be coupled to the final antibody instead of fluorescent probes in the "haptene-antibody sandwich" technique using bifunctional reagents such as glutaraldehyde or in the case of peroxidase via oxidation of the peroxidase carbohydrate moieties to aldehydes and coupling of these residues with ε-amino groups of the desired protein. For the streptavidin-biotinized carrier protein method, an enzyme with biotinyl groups coupled to it could replace a fluorescently-biotinized carrier system. Alternately, the enzyme could be coupled via biotin to the last layer of streptavidin with amplification of streptavidin sites being built up in preceding layers using biotinized BSA or thyroglobulin. We will begin developing the necessary histochemical reagents and the appropriate substrate/insoluble product combinations for visualizing in situ hybridizations without background problems in the near future. The histochemical approaches to signal amplification should therefore be ready for trial in the summer of 1981.

Detecting and/or imaging very low levels of fluorescent light is possible using currently available image intensifiers or systems composed of lasers and photomultipliers. These methods permit the detection of light down to the level of individual photons. With suitable digital processing systems, images can be produced in which each point, i.e. each pixel, of the image is strictly proportional to the number of photons emitted by a point at the object. Using systems of this kind or flow systems in which the cells or parts of cells flow past a laser beam, one can obtain detection sensitivity increases for fluorescent material of factors between 100 and 1000 beyond that which can be detected by the eye. This increase is sufficient to detect the fluorescence of single copy genes.

In a preferred modification, analogs of dUTP and UTP that contain a biotin molecule covalently bound to the C-5 position of the pyrimidine ring through an allylamine linker arm have been synthesized. These biotinyl-nucleotides are efficient substrates for a variety of DNA and RNA polymerases in vitro. DNA containing low levels of biotin substitution (50 molecules or less/kilobase) has denaturation, reassociation and hybridization characteristics which are indistinguishable from that of unsubstituted control DNA.

Thus, this invention also provides a method of chromosomal karyotyping. In this method, modified polynucleotides are prepared which correspond to known genes and include modified nucleotides. These polynucleotides are hybridized with chromosomal deoxyribonucleic acid and the resulting duplexes contacted with appropriate polypeptides under suitable conditions to permit complex formation. The polypeptides include detectable moieties so that the location of the complexes can be determined and the location of specific genes thereby fixed.

Another embodiment of this invention involves detection of poly A-containing sequences using poly U in which some of the uracil bases have been modified to contain a probe. Yet another embodiment involves cyclic modified nucleotides in which two of

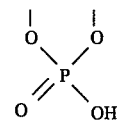

and z are reacted to form the cyclic moiety
Such cyclic modified nucleotides may then be used to identify hormone receptor sites on cell surfaces which in turn can be used as a method of detecting cancer or tumor cells.

Finally, tumor cells can be diagnosed by preparing polynucleotides which are modified according to this invention and are complementary to the messenger ribonucleic acid synthesized from a deoxyribonucleic acid gene sequence associated with the production of polypeptides, such as α-fetal protein or carcinoembryonic antigen, the presence of which is diagnostic for specific tumor cells. Hybridization and detection of hybrid duplexes thus would provide a method for detecting the tumor cells.

The examples which follow are set forth to illustrate various aspects of the present invention but are not intended to limit in any way its scope as more particularly set forth in the claims.

EXAMPLE 1 AND 2

Synthesis of biotinyl—UTP and biotinyl—dUTP a) Preparation of Mercurated Nucleotides UTP (570 mg, 1.0 mmole) or dUTP 554 mg, 1.0 mmole) was dissolved in 100 ml of 0.1M sodium acetate buffer pH 6.0, and mercuric acetate (1.59 gm, 5.0 mmoles) added. The solution was heated at 50° C. for 4 hours, then cooled on ice. Lithium chloride (392 mg, 9.0 mmoles) was added and the solution extracted six times with an equal volume of ethyl acetate to remove excess $HgCl_2$. The efficiency of the extraction process was monitored by estimating the mercuric ion concentration in the organic layer using 4, 4'-bis(dimethylamino)-thiobenzophenone (A. N. Christoper, Analyst, 94, 392 (1969). The extent of nucleotide mercuration, determined spectrophotometrically following iodination of an aliquot of the aqueous solution as described by Dale et al. (R. M. K. Dale, D. C. Ward, D. C. Livingston, and E. Martin, Nucleic Acid Res. 2, 915 [1975]), was routinely between 90 and 100%. The nucleotide products in the aqueous layer, which often became cloudy during the ethyl acetate extraction, were precipitated by the addition of three volumes of ice-cold ethanol and collected by centrifugation. The precipitate was washed twice with cold absolute ethanol, once with ethyl ether, and then air dried. These thus prepared mercurated nucleotides were used for the synthesis of the allylamine-nucleotides without further purification.

b) Synthesis of allylamine—dUTP and allylamine—UTP

The mercurated nucleotides (of step a) were dissolved in 0.1M sodium acetate buffer at pH 5.0, and adjusted to a concentration of 20 mM (200 OD/ml at 267 nm). A fresh 2.0 M solution of allylamine acetate in aqueous acetic acid was prepared by slowly adding 1.5 ml of allylamine (13.3 mmoles) to 8.5 ml of ice-cold 4M acetic acid. Three ml (6.0 mmoles) of the neutralized allylamine stock was added to 25 ml (0.5 mmole) of nucleotide solution. One nucleotide equivalent of $K_2PdCl_4$, (163 mg, 0.5 mmole), dissolved in 4 ml of water, was then added to initiate the reaction. Upon addition of the palladium salt (Alfa-Ventron) the solution gradually turned black with metal (Hg and Pd) deposits appearing on the walls of the reaction vessel. After standing at room temperature for 18–24 hours, the reaction mixture was passed through a 0.45 mm membrane filter (nalgene) to remove most of the remaining metal precipitate. The yellow filtrate was diluted five-fold and applied to a 100 ml column of DEAE-Sephadex TM A-25 (Pharmacia). After washing with one column volume of 0.1M sodium acetate buffer at pH 5.0, the products were eluted using a one liter linear gradient (0.1–0.6M) of either sodium acetate at pH ~8–9, or triethylammonium bicarbonate (TEAB) at pH 7.5. The desired product was in the major UV-absorbing portion which eluted between 0.30 and 0.35M salt. Spectral analysis showed that this peak contained several products, final purification was achieved by reverse phase—HPLC chromatography on columns of Partisil—ODS2, using either 0.5M $NH_4H_2PO_4$ buffer at pH 3.3 (analytical separations), or 0.5M triethylammonium acetate at pH 4.3 (preparative separations) as eluents. The 5'-triphosphates of 5-(3-aminopropen-1-yl) uridine (the allylamine adduct to uridine) were the last portions to be eluted from the HPLC column and they were clearly resolved from three, as yet uncharacterized, contaminants. These nucleotides were characterized by proton NMR elemental analysis [AA-dUTP ($C_{12} H_{16} N_3 O_{14} P_3 Na_4.1H_2O$): theory C, 22.91; H, 2.88; N, 6.68; P, 14.77. Found, C, 23.10; H, 2.85; N, 6.49; P, 14.75. AA-UTP ($C_{12} H_{16} N_3 O_{15} P_3 Na_4.4H_2O$): Theory, C 20.61; H, 3.46; N, 6.01; P, 13.3. Found C, 20.67; H, 4.11; N, 5.39; P, 13.54] spectrally and chromatographically.

c) Biotination of AA-dUTP or AA-UTP

Biotinyl-N-hydroxysuccinimide ester (NHSB) was prepared from biotin (Sigma) as described previously (H. Heitzmann and F. M. Richards, Proc. Natl. Acad. Sci. USA. 71, 3537 [1974]). AA-dUTP·$H_2O$ (63 mg, 0.1 mmole) or AA-UTP·$4H_2O$ (70 mg, 0.1 mmole) was dissolved in 20 ml of 0.1M sodium borate buffer at pH 8.5, and NHSB (34.1 mg, 0.1 mmole) dissolved in 2 ml of dimethyl formamide, was added. The reaction mixture was left at room temperature for four hours and then loaded directly onto a 30 ml column of DEAE-Sephadex TM A-25, preequilibrated with 0.1M TEAB at pH 7.5. The column was eluted with a 400 ml linear gradient (0.1–0.9M) of TEAB. Fractions containing biotinyl-dUTP or biotinyl-UTP, which eluted between 0.55 and 0.65M TEAB, were desalted by rotary evaporation in the presense of methanol and redissolved in water. Occasionally a slightly cloudy solution was obtained: this turbidity, due to a contaminant in some TEAB solutions, was removed by filtration through a 0.45 mm filter. For long term storage, the nucleotides were converted to the sodium salt by briefly stirring the solution in the presence of Dowex TM 50 ($Na^+$ form). After filtration the nucleotide was precipitated by the addition of three volumes of cold ethanol, washed with ethyl ether, dried in vacuo over sodium hydroxide pellets, and stored in a dessicator at −20° C. For immediate use, the nucleotide solution was made 20 mM in Tris-HCl at pH 7.5, and adjusted to a final nucleotide concentration of 5 mM. Stock solutions were stored frozen at −20° C.

Elemental analysis of the bio-dUTP and bio-UTP products yielded the following results. Bio-dUTP ($C_{22} H_{30} N_5 O_{18} P_3 S_1 Na_4.1 H_2O$). Theoretical; C, 29.80; H, 3.38; N, 7.89; P, 10.47; S. 3.61. Found; C, 30.14 H, 3.22; N, 7.63; P, 10.31; S, 3.70. Bic-UTP ($C_{22} H_{30} N_5 O_{19} P_3 S_1 Na_4.3 H_2O$): Theoretical; C, 29.15; H, 3.19; N, 7.45; P, 9.89; S, 3.41. Found; C, 28.76; H, 3.35; N, 7.68; P, 9.81; S, 3.32.

The spectral properties of bio-dUTP and bio-UTP at pH 7.5 [λ max, 289 nm ($\epsilon$=7,100); λ max, 240 nm ($\epsilon$=10,700); λ min, 262 nm ($\epsilon$=4,300)] reflect the presence of an exocylic double-bond in conjugation with the pyrimidine ring. These nucleotides also give a strong positive reaction (an orange-red color) when treated with p-dimethylaminocinnamaldehyde in ethanolic sulfuric acid, a procedure used for biotin quantitation (D. B. McCormick and J. A. Roth, Anal. Biochem., 34, 326, 1970). However, they no longer react with ninhydrin, a characteristic reaction of the AA-dUTP and AA-UTP starting materials.

EXAMPLES 3 AND 4

Synthesis of biotinyl-CTP and biotinyl-dCTP

CTP and dCTP were a) mercurated, b) reacted with allylamine, and c) biotinized with NHS-biotin, essentially as described in Example 1. CTP (56.3 mg, 0.1 mmole) or dCTP (59.1 mg, 0.1 mmole) were dissolved in 20 ml of 0.1M sodium acetate buffer at pH 5.0, and mercuric acetate (0.159 gm, 0.5 mmoles) added. The solution was heated at 50° C. for 4.5 hours then cooled on ice. Lithium chloride (39.2 mg, 0.9 mmoles) was added and the solution extracted 6 times with ethyl acetate. The nucleotide products in the aqueous layer were precipitated by the addition of three volumes of cold ethanol and the precipitate collected by centrifugation. The precipitate was washed with absolute ethanol, ethyl ether, and then air dried. These products were used without further purification for the synthesis of AA-CTP and AA-dCTP, respectively. The mercurated nucleotides were dissolved in 0.1M sodium acetate buffer at pH 5.0 and adjusted to a concentration of 10 mM (92 OD/ml at 275 nm). 0.6 ml (1.2 mmole) of a 2.0M allylamine acetate stock (prepared as described in Example 1) was added to 10 ml of nucleotide solution (0.1 mmole) followed by the addition of $K_2PdCl_4$ (32.6 mg, 0.1 mmole), dissolved in 1.0 ml of $H_2O$. After standing at room temperature for 24 hours, the solution was filtered through a 0.45 mM membrane to remove metal precipates. The filtrate was diluted five-fold and loaded onto a 50 ml. column of DEAE-sephadex A-25, preequilibrated with 50 mM TEAB at pH 7.5. The nucleotide products were fractionated by application of a 500 ml linear gradient (0.05–0.6M) of TEAB at pH 7.5. The desired product was in the major UV absorbing portion which eluted between 0.28 and 0.38M salt. The pooled samples were desalted by rotary evaporation, dissolved in 0.5M triethylammonium acetate at pH 4.2, and final purification achieved by HPLC chromatography on columns of Partisil ODS-2, using 0.5M triethylammonium acetate as the eluent. Appropriate fractions were pooled, lyophilized, and the products dissolved in $H_2O$. The nucleotides were converted to the $Na^+$ salt by stirring briefly in the presence of Dowex TM 50 ($Na^+$ form). After filtration, to remove the Dowex resin, the nucleotides were precipitated by the addition of 3 volumes of cold ethanol. The precipitate was washed with ether and then air dried. Analytical results: AA-dCTP ($C_{12} H_{17} N_4 O_{13} P_3 Na_4.2H_2O$); Theory, C, 22.29; H, 2.63; N, 8.67, P, 14.40. Found C, 22.16; H. 2.89; N. 8.77; P, 14.18. AA-CTP ($C_{12} H_{17} N_4 O_{14} Na_4.2H_2O$); Theory C, 21.75; H, 2.57; N, 8.46; P, 14.01. Found, C, 22.03; H, 2.47; N, 8.69; P, 13.81; Spectral properties in 0.1M Borate buffer at pH 8.0, $\lambda$ max 301 nm ($\epsilon$=6,400), $\lambda$ min 271 nm ($\epsilon$=3,950) $\lambda$ max 250 nm ($\epsilon$=9, 700). Both AA-dCTP and AA-CTP give a positive ninhydrin test. AA-CTP (6.6 mg, 0.01 mmole) or AA-dCTP (6.4 mg, 0.01 mmole) was dissolved in 5 ml of 0.1M sodium borate buffer at pH 8.5, and NHS-biotin (3.4 mg, 0.01 mmole), dissolved in 0.2 ml of dimethylformamide, was added. After sitting at room temperature for 4 hours the sample was chromatographed on a 10 ml column of DEAE-Sephadex A-25, using a 150 ml linear gradient (0.1–0.9M) of TEAB at pH 7.5, as eluent. Fractions containing biotinyl-CTP or biotinyl-dCTP, which eluted between 0.50 and 0.6M TEAB, were pooled, desalted by rotary evaporation, and after being adjusted to a final concentration of 5 mM in 0.02M Tris-HCl buffer at pH 7.5, were frozen at −20° C. The products give a strong positive reaction for biotin with p-dimethylaminocinnamldehyde in ethanolic sulfuric acid but give a negative test for primary amines when sprayed with ninhydrin. Further structural characterization of these products is in progress.

EXAMPLES 5 AND 6

Synthesis of Iminobiotinyl—UTP and Iminobiotinyl—dUTP

Iminobiotin hydrobromide was prepared from biotin as described previously (K. Hofmann, D. B. Melville and V. du Vigneaud, J. Biol. Chem, 141, 207–211, 1941; K. Hofmann and A. E. Axelrod, Ibid., 187, 29–33, 1950). The N-hydroxysuccinimide (NHS) ester of iminobiotin was prepared using the protocol previously described for the synthesis of NHS-Biotin (H. Heitzmann and F. M. Richards, Proc. Nat. Acad. Sci. USA, 71, 5537, 1974). AA-UTP (7.0 mg, 0.01 mmole) or AA-dUTP (6.3 mg, 0.01 mmole), prepared as detailed in example 1 (part b), was dissolved in 5 ml of 0.1M sodium borate buffer at pH 8.5, and NHS-iminobiotin (3.5 mg, 0.01 mmole), dissolved in 0.5 ml of dimethylformamide, was added. The reaction mixture was left at room temperature for 12 hours and then loaded directly onto a 10 ml column of DEAE-Sephadex A-25, preequilibrated with 0.05M TEAB at pH 7.5. The column was eluted with a 150 ml linear gradient (0.05–0.6M) of TEAB. Fractions containing iminobiotin-UTP or iminobiotin-dUTP, which eluted between 0.35 and 0.40M TEAB, were desalted by rotary evaporation in the presence of methanol and dissolved in $H_2O$. The products contained a small amount of allylamine-nucleotide adduct as an impurity, as judged by a weak positive result in the ninhydrin test. Final purification was achieved by affinity chromatography on avidin-sepharose. Fractions of the impure product, made 0.1M in soldium borate buffer at pH 8.5, were applied to a 5 ml column of avidin-sepharose and washed with 25 ml of the same buffer. The column was then washed with 50 mM ammonium acetate buffer at pH 4.0, which eluted the desired iminobiotin-nucleotide product in a sharp peak. The nucleotide was precipitated by the addition of 3 volumes of cold ethanol, washed with ethylether, dried in vacuo over sodium hydroxide pellets and stored in a dessicator at −20° C. Products were characterized by elemental analysis, as well as by spectral and chromotographic properties.

EXAMPLES 7 AND 8

Synthesis of NAGE—UTP and NAGE—dUTP

Allyl (3-amino-2-hydroxy,)propyl ether, abbreviated NAGE, was prepared from allyl glycidyl ether (Age) (obtained from Aldrich Chemical Co. ). 10 ml of Age (84 mmole) was added slowly (in a fume hood) to 50 ml of 9M ammonium hydroxide and the mixture allowed to stand at room temperature for six hours. Excess ammonia was removed by rotary evaporation under reduced pressure to yield a viscous yellow oil. Analysis of this product by proton NMR showed that it possessed the required structure. 5-mercuri-dUTP (0.1 mmole) or 5-mercuri-UTP (0.2 mmole) was dissolved in 2–4 ml of 0.2M sodium acetate buffer at pH 5.0, and a 16 fold molar excess of NAGE adjusted to pH 5.0 with acetic acid prior to use, was added. The final reaction volumes (4.3 and 8.4 ml) had nucleotide concentrations of 43 and 42 mM, respectively. One equivalent of $K_2PdCl_4$ (0.1 or 0.2 mmoles) was added to initiate the reaction. After standing at room temperature for 18 hours, the reaction mixtures were filtered through 0.45 µmM membranes the samples diluted five-fold, and chromatographed on columns of DEAE-Sephadex A-25, using linear gradients (0.1–0.6M) of sodium acetate. Fractions containing the desired products, as judged by their UV spectra and characteristic HPLC elution profiles on Partisil ODS-2, were pooled, diluted, and further purified by rechromatography on DEAE-Sephadex using shallow gradients (0.1–0.5M) of ammonium bicarbonate at pH 8.5. Under these conditions the majority of the NAGE-dUTP (or NAGE-UTP)could be cleanly separated from residual impurities. Proton NMR spectra were obtained at this stage of purification after the nucleotides were lyophilized and redissolved in $D_2O$. For elemental analysis, the products were converted to their sodium salt form. Typical analytical results: Nage-dUTP ($C_{15} H_{22} N_3 O_{16} P_3 Na_4.2 H_2O$), Theory, C, 24.99; H, 3.63; N, 5.83; P, 12.88. Found, C, 25.39; H, 3.71; N, 5.63; P, 12.88

EXAMPLE 9

Uses of Labeled DNA Sequences

I, Karyotyping (a) select from a human gene library some 100 to 200 clones. Label them as described above, and for each clone locate its place or places of hybridization visually or with a low-light-level video system. For those clones which correspond to a unique sequence gene this determines the location of the cloned DNA on a particular human chromosome. Obtain several clones for each chromosome. Each of these labeled clones can be used to identify particular chromosomes. They can also be used in combination to identify each of the 46 chromosomes as being one of the 22 autosomal pairs or the X or the Y. By allowing one set of labeled clones to hybridize to the chromosomes and then adding a fluorescent stain to the label, the set of clones and their locations can be visualized and will fluoresce with a particular color. A second set of labeled clones could then be used and reacted with a second fluorescent dye. The same process can be repeated a number of times. Thus one can, if desired, have several sets of fluorescent labels attached to the cellular DNA at different but specific locations on each of the chromosomes. These labels could be used for visual or computerized automatic karyotyping.

(b) For automatic karyotyping, one could use one set of clones to identify the approximate location of each of the 46 chromosomes by finding sets of spots corresponding to the number of labeling sites on each chromosome. Thus, it is possible by computer analysis of the digitized images to determine if the chromosomes are suitably spread for further analysis. If they are suitably spread then one can use computer analysis to identify each of the individual chromosomes by the location and distribution of the labelled spots on each one.

By using the fact that the fluorescent spots can be placed at specific locations on each chromosome, one can carry out either manual or automatic karyotyping very much more effectively than without such labels.

II. Diagnosis of Genetic Disorders

By selecting the clones which bind specifically to a particular chromosome, such as number 23, it is possible to count the number of copies of the particular chromosome in a cell even if the chromosomes are not condensed at metaphase. Thus when fetal cells are obtained for prenatal diagnosis of trisomy 21, the diagnosis can be done even if the chromosomes are not condensed at metaphase. If necessary, two sets of labels can be used— one which would be specific for chromosome 23 and one for some other chromosome. By measuring in each cell the ratio of the two labels, which might be of different colors, it is possible to identify the cells which show an abnormal number of chromosomes number 23. This procedure could be used either on slides with a low-light-level video system or in a flow cytometer system using laser excitation. It can be used to determine any abnormal chromosome number.

III. Microorganism Detection and Identification

The labeling of specific sequences of DNA as described above permits identification and counting of individual bacteria. In order to identify the individual bacteria to which a particular fragment of DNA hybridizes the sensitivity must be such that a single labelled structure can be detected. This can be done using a low-light-level video system and computer summation of images, or by using some other device for intensifying the light image. A flow system can also be used if the sensitivity can be made sufficiently grand. If one immobilized the bacteria on a slide their location could be found and the number of such fluorescent spots counted. This would provide a count of all of those bacteria which contain DNA which can hybridize with the specific clone utilized. If the clone is selected as being specific for a particular strain or bacteria, then one can count the number of organisms of that strain. In addition, any antibiotic resistance for which a particular gene has been identified could be characterized in a similar way using, as a probe, the DNA sequence which is contained in the antibiotic resistance gene. In addition, a probe could be used which is specific for a resistance plasmid containing one or more antibiotic resistance genes. In addition to individual bacteria, groups of bacterial cells of a particular strain can be detected and their number estimated if they are located in a small spot so that the total fluorescence specific to the hybridized DNA in the spot can be measured. In this way the number of organisms containing a specific DNA sequence can be measured in a mixture of bacteria.

We claim:

1. A compound useful as a probe for detecting the presence or absence of a nucleic acid, said compound having the structure:

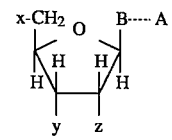

wherein B represents a purine, 7-deazapurine, or pyrimidine moiety suitable for incorporation into a polynucleotide and covalently bonded to the $C^{1'}$-position of the sugar moiety, provided that when B is a purine or 7-deazapurine, the sugar moiety is attached at the $N^9$-position of the purine or deazapurine, and when B is pyrimidine, the sugar moiety is attached at the $N^1$ position of the pyrimidine;

wherein A represents at least three carbon atoms and an indicator molecule selected from the group consisting of fluorescent dyes, electron-dense reagents, enzymes which can be reacted with a substrate to produce a visually detectable reaction product, and radioisotopes;

wherein B and A are covalently attached directly or through a linkage group, said linkage group not interfering substantially with detection of A;

wherein if B is a purine, A is attached to the 8-position of the purine, if B is a 7-deazapurine, A is attached to the 7-position of the deazapurine, and if B is a pyrimidine, A is attached to the 5-position of the pyrimidine; and wherein each of x, y and z represents:

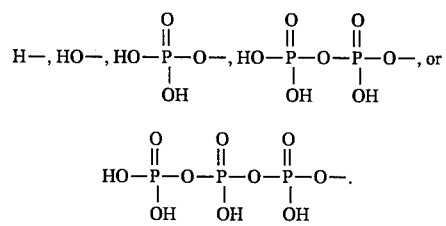

2. A compound useful as a probe for detecting the presence or absence of a nucleic acid, said compound containing a nucleotide having the structure:

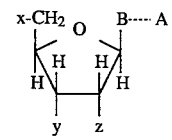

wherein B represents a purine, 7-deazapurine, or pyrimidine moiety covalently bonded to the $C^{1'}$-position of the sugar moiety, provided that whenever B is purine or 7-deazapurine, the sugar moiety is attached at the $N^9$-position of the purine or deazapurine, and whenever B is a pyrimidine, the sugar moiety is attached at the $N^1$-position of the pyrimidine;

wherein A represents at least three carbon atoms and an indicator molecule selected from the group consisting of fluorescent dyes, electron-dense reagents, enzymes which can be reacted with a substrate to produce a visually detectable reaction product and radioisotopes;

wherein B and A are covalently attached directly or through a linkage group, said linkage group not interfering substantially with detection of A;

wherein if B is a purine, A or the linkage group is attached to the 8-position of the purine, if B is a 7-deazapurine, A or the linkage group is attached to the 7-position of the deazapurine, and if B is a pyrimidine, A or the linkage group is attached to the 5-position of the pyrimidine;

wherein one of x and y represents

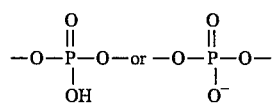

and the other of x and y is absent or represents —OH or —H; and wherein z represents H— or HO—.

3. A complex useful as a probe for detecting the presence or absence of a nucleic acid, said complex comprising a detectable polypeptide complexed with a compound having the structure:

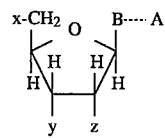

wherein B represents a purine, 7-deazapurine, or pyrimidine moiety suitable for incorporation into a polynucleotide and covalently bonded to the $C^{1'}$-position of the sugar moiety, provided that when B is a purine or 7-deazapurine, the sugar moiety is attached at the $N^9$-position of the purine or deazapurine, and when B is pyrimidine, the sugar moiety is attached at the $N^1$ position of the pyrimidine;

wherein A represents at least three carbon atoms, is capable of specifically complexing with the detectable polypeptide when A is linked to B, and represents a component of a signalling moiety capable of producing a detectable signal;

wherein B and A are covalently attached directly or through a linkage group, said linkage group not interfering substantially with the characteristic ability of A to form said complex with the detectable polypeptide;

wherein if B is a purine, A is attached to the 8-position of the purine, if B is a 7-deazapurine, A is attached to the 7-position of the deazapurine, and if B is a pyrimidine, A is attached to the 5-position of the pyrimidine; and wherein each of x, y and z represents:

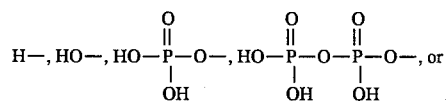

-continued

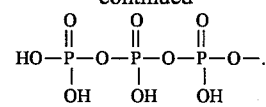

4. A complex in accordance with claim 3 wherein said detectable polypeptide is linked to an indicator molecule selected from the group consisting of fluorescent dyes, electron-dense reagents, enzymes which can be reacted with a substrate to produce a visually detectable reaction product, and radioisotopes.

5. A complex in accordance with claim 4 wherein said detectable polypeptide is a fluorescent dye, electron dense reagent, or enzyme which can be reacted with a substrate to produce a visually detectable reaction product.

6. A complex useful as a probe for detecting the presence or absence of a nucleic acid, said complex comprising a detectable polypeptide complexed with an oligo- or polynucleotide containing a nucleotide having the structure:

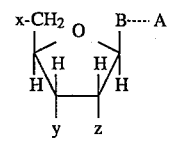

wherein B represents a purine, 7-deazapurine, or pyrimidine moiety covalently bonded to the $C^{1'}$-position of the sugar moiety, provided that whenever B is purine or 7-deazapurine, the sugar moiety is attached at the $N^9$-position of the purine or deazapurine, and whenever B is a pyrimidine, the sugar moiety is attached at the $N^1$-position of the pyrimidine;

wherein A represents at least three carbon atoms, is capable of specifically complexing with the detectable polypeptide when A is linked to B, and represents a component of a signalling moiety capable of producing a detectable signal;

wherein B and A are covalently attached directly or through a linkage group, said linkage group not interfering substantially with the characteristic ability of A to form said complex with the detectable polypeptide;

wherein if B is a purine, A or the linkage group is attached to the 8-position of the purine, if B is a 7-deazapurine, A or the linkage group is attached to the 7-position of the deazapurine, and if B is a pyrimidine, A or the linkage group is attached to the 5-position of the pyrimidine;

wherein one of x and y represents

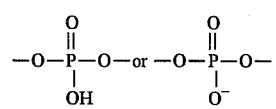

and the other of x and y is absent or represents —OH or —H; and wherein z represents H— or HO—.

7. A complex in accordance with claim 6 wherein said detectable polypeptide is linked to an indicator molecule selected from the group consisting of fluorescent dyes, electron-dense reagents, enzymes which can be reacted with a substrate to produce a visually detectable reaction product, and radioisotopes.

8. A complex in accordance with claim 7 wherein said detectable polypeptide is a fluorescent dye, electron dense reagent, or enzyme which can be reacted with a substrate to produce a visually detectable reaction product.

9. A complex in accordance with claims 3 or 6 wherein A is a ligand.

10. A complex according to claim 9 wherein said ligand is selected from the group consisting of biotin, iminobiotin, or a cofactor.

11. A complex in accordance with claim 9 wherein said ligand is selected from the group consisting of antigens, antibodies and haptens.

12. A complex in accordance with claim 11 wherein said ligand is dinitrophenol.

13. A complex according to claims 3 or 6 wherein the detectable polypeptide is indirectly detectable by specifically complexing the detectable polypeptide with a second moiety covalently linked to an indicator molecule selected from the group consisting of fluorescent dyes, electron-dense reagents, enzymes which can be reacted with a substrate to produce a visually detectable reaction product, and radioisotopes.

14. A complex according to claim 13 wherein the detectable polypeptide is selected from the group consisting of avidin and streptavidin and the second moiety is selected from the group consisting of biotin and iminobiotin.

15. A complex according to claim 14 wherein the indicator molecule is an enzyme which can be reacted with a substrate to produce a visually detectable reaction product.

16. The complex of claims 3 or 6 wherein said linkage group is comprises a —$CH_2$—NH—.

17. The complex of claims 3 or 6 wherein said linkage group is selected from the group consisting of —CH=CH—$CH_2$—NH— and —CH=CH—$CH_2$—O—$CH_2$—CH(OH)—$CH_2$—NH—.

18. The complex of claims 3 or 6 wherein A is an allylamine group linked directly to B.

19. The complex of claims 3 or 6 wherein A is a moiety comprising an olefinic bond.

* * * * *